US009925529B2

(12) United States Patent
Balikhin et al.

(10) Patent No.: US 9,925,529 B2
(45) Date of Patent: Mar. 27, 2018

(54) PHOTOCATALYTIC ELEMENT FOR PURIFICATION AND DISINFECTION OF AIR AND WATER AND METHOD FOR THE PRODUCTION THEREOF

(71) Applicants: OOO "KRASNOE POLE", Moscow region (RU); IPKHF RAN, Chernogolovka (RU); NTSCHRAN, Chernogolovka (RU); OOO "TIOKRAFT", Chernogolovka (RU)

(72) Inventors: Igor Lvovich Balikhin, Chernogolovka (RU); Victor Ivanovich Berestenko, Chernogolovka (RU); Igor Anatolevich Domashnev, Chernogolovka (RU); Evgeny Nikolaevich Kabachnikov, Chernogolovka (RU); Evgeny Nikolaevich Kurkin, Chernogolovka (RU); Vladimir Nikolaevich Troitsky, Chernogolovka (RU)

(73) Assignees: OOO "Krasnoe Pole", Moscow Region (RU); Ipkhf Ran, Chemogolovka (RU); Ntschian, Chemogolovka (RU); OOO "Tiokraft", Chemogolovka (RU)

( * ) Notice: Subject to any disclaimer, the term of this patent is extended or adjusted under 35 U.S.C. 154(b) by 450 days.

(21) Appl. No.: 14/768,119

(22) PCT Filed: Dec. 20, 2012

(86) PCT No.: PCT/RU2012/001086
§ 371 (c)(1),
(2) Date: Aug. 14, 2015

(87) PCT Pub. No.: WO2014/098641
PCT Pub. Date: Jun. 26, 2014

(65) Prior Publication Data
US 2016/0008804 A1    Jan. 14, 2016

(51) Int. Cl.
*A61L 9/00* (2006.01)
*B01J 35/00* (2006.01)
(Continued)

(52) U.S. Cl.
CPC ........ *B01J 35/004* (2013.01); *B01D 53/8668* (2013.01); *B01D 53/885* (2013.01);
(Continued)

(58) Field of Classification Search
CPC .. B01J 35/004; B01J 35/1076; B01J 35/1019; B01J 35/10; B01J 35/00; B01J 21/063;
(Continued)

(56) References Cited

FOREIGN PATENT DOCUMENTS

| RU | 2151632 | * | 6/2000 |
| RU | 98134 | * | 10/2010 |
| WO | WO 1996037300 | * | 11/1996 |

OTHER PUBLICATIONS

RU2151632, Troitskij et al, see machine translation, 2000.*
RU98134 Balikhin et al, see machine translation, 2010.*

\* cited by examiner

*Primary Examiner* — Melvin C Mayes
*Assistant Examiner* — Smita Patel
(74) *Attorney, Agent, or Firm* — Galgano IP Law PLLC; Thomas M Galgano; Jessica G. McDonald

(57) ABSTRACT

The invention relates to the purification and disinfection of air and water. A photocatalytic element consists of sintered glass beads with a pore volume fraction from 20% to 40% and a pore size from 0.1 to 0.5 mm, the surface of which is coated with a titanium dioxide powder, having a specific surface area of 150-400 $m^2/g$, at the rate of 0.5-2% relative to the total mass of the photocatalytic element. The surface of the glass beads has a relief shape with a relief depression of 0.5-10 μm. The method for producing the photocatalytic
(Continued)

Figure 1:

element comprises sintering the glass beads at a temperature that is 5-20° C. higher than the glass softening temperature, modifying the bead surface with chemical etching agents, and coating the bead surface with the titanium dioxide powder from a water suspension at a pH of 2.9±0.1.

3 Claims, 2 Drawing Sheets

(51) Int. Cl.
    *B01D 53/86*     (2006.01)
    *B01D 53/88*     (2006.01)
    *B01J 21/06*     (2006.01)
    *B01J 35/10*     (2006.01)
    *B01J 37/02*     (2006.01)
    *C02F 1/72*     (2006.01)
    *A61L 9/20*     (2006.01)
    *B01J 37/06*     (2006.01)
    *B01J 37/08*     (2006.01)

(52) U.S. Cl.
CPC ............. *B01J 21/063* (2013.01); *B01J 35/10* (2013.01); *B01J 35/1019* (2013.01); *B01J 35/1076* (2013.01); *B01J 37/0217* (2013.01); *C02F 1/725* (2013.01); *A61L 9/205* (2013.01); *B01D 2255/20707* (2013.01); *B01D 2255/802* (2013.01); *B01D 2255/9202* (2013.01); *B01D 2255/9205* (2013.01); *B01D 2255/9207* (2013.01); *B01D 2257/704* (2013.01); *B01D 2257/90* (2013.01); *B01D 2257/91* (2013.01); *B01D 2258/06* (2013.01); *B01D 2259/4508* (2013.01); *B01D 2259/4533* (2013.01); *B01D 2259/804* (2013.01); *B01J 37/06* (2013.01); *B01J 37/08* (2013.01); *C02F 2303/04* (2013.01); *C02F 2305/10* (2013.01)

(58) Field of Classification Search
CPC ........ B01J 21/06; B01J 37/08; B01J 37/0217; B01J 37/06; C02F 1/725; B01D 53/8668; B01D 53/885; B01D 2255/20707; B01D 2255/802; B01D 2255/9202; B01D 2255/9207; B01D 2257/704; B01D 2257/90; B01D 2257/91; B01D 2258/06; B01D 2259/4508; B01D 2259/4533; B01D 2259/804; A61L 9/00; A61L 9/205
See application file for complete search history.

PHOTOCATALYTIC ELEMENT FOR PURIFICATION AND DISINFECTION OF AIR AND WATER AND METHOD FOR THE PRODUCTION THEREOF

This invention relates to the field of purification and disinfection of air and water, and particularly to the design of and method for the production of a photocatalytic element that may be used as a primary functional unit in molecular and integrated treatment devices utilizing photocatalysis.

Photoactivated catalytic oxidative destruction of organic pollutants with the use of titanium dioxide and under the action of ultraviolet light is an advanced method for air and water purification and disinfection. This method is efficient, cost-effective, environmentally-friendly and allows elimination of almost any organic pollutants by mineralizing them to water and carbon dioxide. The primary functional unit of photocatalytic treatment devices that ensures their efficiency and durability is a photocatalytic element in the form of structure combining a nanocrystalline catalyst and a carrier of defined shape installed in the UV radiation coverage zone.

The photocatalytic element may be used as part of air purification and disinfection devices employed in healthcare facilities, child daycare centers, schools, offices, cinemas, living spaces, etc. for effective control of respiratory infections, toxic pollutant and offensive odor elimination.

Known is a method for producing a photocatalytic material (U.S. Pat. No. 5,919,726; Date of Patent: Jul. 6, 1999), the first stage of which consists in the application anywise (spraying, brushing, etc.) on a substrate made from any material (metal, cement, clay, sand, gravel, ceramic, plastic, wood, stone, glass, etc.) of a sub-layer with a thickness of 0.05 to 2 micron containing silica gel with approximate particle size of 20 to 50 micron, which sub-layer is then fixed by heat treatment at 100 to 900° C. during 3 to 30 minutes. At the second stage, the sub-layer is treated by liquid or vaporous titanium tetrachloride (water vapor may be added). At the third state, the obtained material is heat-treated at 150 to 500° C. in the presence of oxygen during 1 to 10 minutes as a result of which an anatase titanium dioxide layer is formed on the surface. Due to the presence of the silica sub-layer, the resulting titanium dioxide is fixed on the substrate and retains its photocatalytic properties. This method is recommended primarily for the manufacture of building materials with photocatalytic air purification and disinfection effect (ceramic tiles, wall panels, etc.).

Bactericidal activity tests included application of cell suspension (0.5 ml) on the produced ceramic tiles. The tiles were put in a Petri dish and covered with a quartz glass cap. Incubation was done in a sterile chamber under 1200 lux fluorescent lighting at 25° C. during 3 hours. The results are given in Table 2. For reference, a tile without titanium dioxide layer was also subjected to testing. The best of the test specimens demonstrated reduction in the concentration of *Staphylococcus aureus* living cells from 3100 to 135 and that of *Klebsiella pneumonia* from 1725 to 400.

The principal disadvantage of the above photocatalytic material production method is a complex and environmentally hazardous production process associated with the use of highly volatile and toxic titanium tetrachloride. Furthermore, during the titanium dioxide layer application, toxic and corrosive hydrogen chloride is produced as a result of $TiCl_4$ hydrolysis.

Bactericidal activity of the produced material specimens is not sufficient for the application in air purification and disinfection devices.

Known is a photocatalytic air treatment filter (U.S. Pat. No. 6,491,883 B2; Date of Patent: Dec. 10, 2002). The filter consists of a substrate with a 5 to 60 micron thick coating comprising:

Particles permitting ultraviolet light through (such as glass particles or fibers) with the smallest size of 0.2 to 50 micron in the amount of 5 to 60% by weight;

Photocatalytic $TiO_2$ particles with an average size of 0.001 micron to 0.02 micron in the amount of 20 to 80% by weight;

Silicon dioxide particles with an average size of 0.002 to 0.2 micron in the amount of 10 to 60% by weight;

Optionally, a clay mineral in the amount of 2 to 20% by weight.

The coating features good adhesion to the substrate material and can transmit ultraviolet light, however, the use of finely divided components, in particular those with a clay binder, does not allow ensuring good gas permeability of the coating or effective performance of the photocatalytic $TiO_2$ particles contained within the coating. To produce a photocatalytic element of air and water purification and disinfection devices, a material with high open porosity is required to ensure unobstructed diffusion of the medium being treated to the photocatalyst.

Known is an air purification system for transport vehicles (United States, Patent Application Publication, Pub. No.: US 2012/0128539 A1, Pub. Date: May 24, 2012). The system consists of an air inlet, air outlet and a space for air flow between them. One or more elements with a response surface and one or more ultraviolet light sources are installed in the space. The response surface contains a catalytic material and occupies at least 50% of the device's inner surface. Titanium dioxide or a material containing it is used as the catalytic material. Luminescent tubes or light-emitting diodes are used as the ultraviolet light sources. Air is squeezed through the device's space by a fan. To increase the surface area and time of air contact with the response surface it is proposed to use various shapes of elements fixed within the filter casing, e.g. corrugated, spiral, stellar, finger, and elements in the form of loose material (e.g., short glass or plastic tubes, balls), filling the entire space through which air flows. To further improve air purification efficiency, the elements' response surface may contain nano-zeolites and/or nano-silver. Use of loosely poured elements covered with catalyst provides a large response surface contacting with air being treated, however, non-fixed elements may migrate with respect to each other, inevitably leading to mechanical wear of the catalytic bed due to friction and dust escape from the device, as well as the catalyst service life shortening. Efficient performance of the device requires a consolidated photocatalytic element with high inner porosity and gas permeability. The catalyst must be applied on the carrier's entire surface, including the inner pores' surface.

The most similar combination of essential features to the claimed invention has a photocatalytic element and a method for producing of the same (Russian Federation Patent No. 2151632 dated 20 Oct. 1998), containing a porous carrier of defined shape (preferably, in the form of a tube or a plate) made from 5 to 10 layers of sintered glass beads and anatase titanium dioxide powder with a specific surface area of 100 to 150 м2/g applied onto the carrier's surface. Such photocatalytic element production method includes:

Production of the defined form carrier by sintering glass beads 0.1 to 1.5 mm in diameter at a temperature below the glass softening point in a shell made from metal, graphite or fragile material, cooling, carrier removing from the shell, carrier surface activation with hydrofluoric acid vapors or 1 to 2% solution, application of titanium dioxide powder from aqueous suspension onto the carrier's surface, and air drying of the carrier.

The above photocatalytic element and the method for production of the same have the following disadvantages:

Due to the fact that the glass beads are sintered at a temperature below the glass softening point, the resulting photocatalytic element does not have sufficient mechanical strength, therefore there is a large percentage of photocatalytic element destruction during photocatalytic device transportation, assembly and operation;

Insufficiently high specific surface area of the used titanium dioxide powder (100 to 150 m$^2$/g) restricts the maximum achievable activity of the photocatalytic element in air and water purification processes;

Carrier surface activation by the above method (treatment with hydrofluoric acid vapors or 1 to 2% solution) is not adequately efficient for improving the strength of titanium dioxide powder bonding with the glass beads, specifically for the photocatalytic elements used in water purification devices. During photocatalytic element operation in water streams, part of the titanium dioxide powder is removed from the carrier's surface resulting in decreased activity and shorter service life of the photocatalytic element;

Lack of control over the aqueous suspension pH during the titanium dioxide application onto the carrier does not allow sustainable production of photocatalytic elements of maximum activity.

The object of the present invention is to provide a new photocatalytic element featuring:

enhanced mechanical strength;
increased catalytic activity;
extended service life.

The object is achieved by providing the photocatalytic air and water purification and disinfection element with the following:

porous carrier with defined shape, pore size of 0.1 mm to 0.5 mm, with a pore volume fraction from 20% to 40%, consisting of sintered glass beads having a surface relief depth of 0.5 to 5 micron, and titanium dioxide powder with a specific surface area of 150 to 400 m$^2$/g applied onto the glass surface in the amount of 0.5 to 2% of the total photocatalytic element weight.

The object is also achieved by providing a photocatalytic element that includes:

Fabrication of the carrier by sintering glass beads in a shell giving the required shape and size to the carrier at a temperature 5 to 20° C. above the glass softening point;

Carrier cooling and removal from the shell;

Formation of the carrier's glass surface relief with a depth of 0.5 to 5 micron by treatment of the carrier with concentrated hydrofluoric acid during 1 to 5 minutes followed by concentrated sulfuric acid during 1 to 5 minutes;

Carrier rinsing with water and drying in a drying oven at a temperature of 80 to 120° C.;

Coating the sintered beads' glass surface with titanium dioxide powder with a specific surface area of 150 to 400 m$^2$/g in the amount of 0.5 to 2% of the total photocatalytic element weight by applying aqueous suspension of titanium dioxide with pH=2.9±0.1 onto the carrier.

Drying of the finished photocatalytic element in a drying oven at a temperature of 150 to 200° C.

Glass bead sintering at a temperature 5 to 20° C. above the glass softening point allows providing high mechanical strength of the carrier while retaining high open porosity (20% to 40% of 0.1 to 0.5 mm pores).

Sintered glass bead surface modification by concentrated hydrofluoric acid and sulfuric acid solutions enables providing a glass surface relief depth of 0.5 to 5 micron ensuring strong titanium dioxide powder bonding to and retention at the carrier surface in a stream of air or water being purified. The below figure shows photomicrographs of the sintered beads' surface before (1) and after (2) acid treatment. Such relief is not achieved by conventional surface activation by vapors or dilute hydrofluoric acid solutions.

FIG. 1 shows the carrier surface before (1) and after (2) acidic modification.

When applying titanium dioxide powder onto the carrier surface, the most important factor determining the final activity of a photocatalytic element is the pH value of aqueous suspension from which the powder is applied. The maximum activity is achieved at pH=2.9±0.1. In view of the extreme dependency of photocatalyst activity on the pH value of the medium (FIG. 2), the specified acidity of the suspension (pH=2.9±0.1) must be strictly followed during the titanium dioxide powder application. This technique in combination with the use of titanium dioxide powder with high specific surface area (150 to 400 m$^2$/g) allows producing photocatalytic elements of maximum activity.

Figure 2:
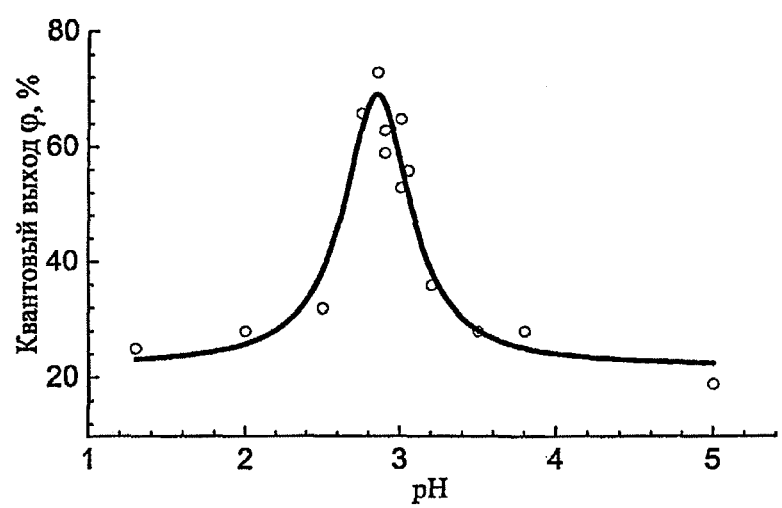

FIG. 2 shows photocatalytic activity of titanium dioxide as a function of the suspension's pH value.

Essence of the present invention is illustrated by the following embodiments.

Embodiment 1

Glass beads (0.8 to 1 mm fraction) are poured to fill up a cylinder-shaped dismountable stainless steel shell with the outer diameter of 86 mm, width of 6 mm and height of 420 mm. The shell is put into an oven where sintering of the beads is done at a temperature 15° C. above the glass softening point (approximately 690° C.) during 1 hour 20 minutes. After cooling to room temperature, the shell is disassembled and the resulting carrier in the form of a porous glass tube is removed.

The carrier surface is then modified by submersion first into concentrated hydrofluoric acid for 1 minute followed by rinsing with water and treatment with concentrated sulfuric acid during 3 minutes, rinsing with water and drying in drying oven at 100° C. until completely dehydrated.

Aqueous suspension is made from distilled water and anatase titanium dioxide powder with specific surface area of 350 M2/g and titanium dioxide content of 10% by weight. Adding dilute sulfuric acid by drops, the suspension's pH value is brought to 2.9±0.1. The dried carrier is submerged in the resulting suspension, removed and dried in a drying oven at 150° C.

The finished photocatalytic element contains:

A porous tubular carrier consisting of sintered glass beads with modified surface, 420 mm long, 86 mm in diameter and with the wall thickness of 6 mm;

Anatase titanium dioxide powder with the specific surface of 350 m$^2$/g in the amount of 12 g per element.

One more photocatalytic element was produced as a reference sample. The production procedure of this sample was different only in that no surface modification operations were performed. No relief was observed on the beads' surface. Titanium dioxide content in the finished photocatalytic element was 10 g.

The samples produced according to this embodiment (the primary No. 1 and the reference No. 2) were subjected to testing in the process of purification of water containing collibacillus (*Escherichia coli*) culture. According to the test pattern, water containing *Escherichia coli* cells was circulated through the vertically installed photocatalytic element's wall at the flow rate of 2 l/min. An ultraviolet lamp was installed inside the tube to illuminate the inner surface of the photocatalytic element with ultraviolet light with a wave length of 320 to 405 nanometers, with 9 W power in the infrared band. Water samples were taken at specified intervals of time and applied on a culture medium in Petri dishes. The number of colonies grown in the culture medium was calculated after 48 hours. Furthermore, titanium dioxide entrainment by the water stream was checked after 10 hours of continuous water flow by measuring the dried photocatalytic element weight. The measurement results are given in Table 1.

TABLE 1

| Treatment Time (minutes) | CFU Concentration | | Weight Loss (g) | |
|---|---|---|---|---|
| | Sample 1 | Sample 2 | Sample 1 | Sample 2 |
| 0 | 10000 | 10000 | 0 | 0 |
| 5 | 5950 | 7250 | — | — |
| 10 | 90 | 750 | — | — |
| 30 | 0 | 50 | — | — |
| 60 | 0 | 0 | — | — |
| 600 | 0 | 0 | 0.3 | 2.1 |

| Table 1 Treatment Time | Acetone Concentration (ppm) | CO2 Concentration (ppm) |
|---|---|---|

The testing results show that modification of the carrier with giving the glass surface a profiled shape increases the titanium dioxide powder capturing when applied from the suspension, provides stronger bonding of the catalyst to the carrier and enhances overall photocatalytic activity of the photocatalytic element.

Embodiment 2

Glass beads (0.8 to 1 mm fraction) are poured to fill up a flat conduit in a dismountable stainless steel shell with the length of 60 mm, width of 5 mm and height of 400 mm. Further sintering, carrier surface modification and catalyst application operations are performed in the same manner as in Embodiment 1.

The finished photocatalytic element contains:

A porous carrier in the form of a parallelepiped with the dimensions of 400☐60☐5 mm, consisting of sintered glass beads with modified surface;

Anatase titanium dioxide powder with the specific surface of 350 $m^2/g$ in the amount of 2 g per element.

A reference test sample was produced in the same manner, except that the titanium dioxide powder was applied on the carrier from a suspension with pH=4.5.

TABLE 2

| Table 1 Treatment Time | Acetone Concentration (ppm) | | CO2 Concentration (ppm) | |
|---|---|---|---|---|
| (minutes) | Sample 1 | Sample 2 | Sample 1 | Sample 2 |
| 0 | 100 | 100 | 0 | 0 |
| 5 | 91 | 93 | 19 | 15 |
| 10 | 82 | 86 | 41 | 29 |
| 30 | 53 | 61 | 104 | 84 |

The samples produced according to this embodiment (the primary No. 3 and the reference No. 4) were tested under the reaction of photocatalytic oxidation of acetone vapors in air. The test was performed in a sealed box with the volume of 300 l, in which a reaction vessel with the subject sample, an ultraviolet lamp analogous to that employed in Embodiment 1, and a fan providing air motion were installed. The initial vapor concentration was produced by evaporation of the required amount of liquid acetone and amounted to 100 ppm. After the UV lamp was turned on, concentration of acetone and that of its oxidation end product (CO2) were measured over time by gas sensors. The test results are given in Table 2.

The results demonstrate greater catalytic activity of Sample 1 on which titanium dioxide had been deposited from the suspension with pH=2.9±0.1.

The invention claimed is:

1. A photocatalytic element for air and water purification and disinfection comprising:
    sintered glass beads covered with titanium dioxide powder, wherein the sintered glass beads have open porosity with a pore size of 0.1 mm to 0.5 mm with a pore volume fraction from 20% to 40%;
    the sintered glass beads' surface has a relief shape with a relief depth of 0.5 to 10 micron; and
    titanium dioxide powder specific surface area is 150 to 400 $m^2/g$ with a weight percentage of the titanium dioxide powder of 0.5 to 2% of the photocatalytic element's weight.

2. A method for the production of the photocatalytic element according to claim 1, comprising:
    sintering of glass beads, sintered glass beads' surface modification, and titanium dioxide powder application on the sintered glass beads' modified surface, wherein the glass beads are sintered at a temperature 5 to 20° C. above the glass softening point, and prior to the titanium dioxide powder application the sintered glass beads' surface is modified by etching chemicals, and the titanium dioxide powder is applied onto the sintered glass beads' surface from a titanium dioxide powder aqueous suspension with the pH value=2.9±0.1.

3. The method for the production of the photocatalytic element according to claim 2, wherein:
    modification of the sintered glass beads' surface by etching chemicals consists in consecutive treatment with concentrated hydrofluoric acid during 1 to 5 minutes and concentrated sulfuric acid during 1 to 5 minutes.

\* \* \* \* \*